(12) United States Patent
Schuelke et al.

(10) Patent No.: US 11,754,075 B2
(45) Date of Patent: Sep. 12, 2023

(54) IMPELLER FOR AN IMPLANTABLE, VASCULAR SUPPORT SYSTEM

(71) Applicant: KARDION GMBH, Stuttgart (DE)

(72) Inventors: Armin Schuelke, Aidlingen (DE); Ingo Stotz, Ditzingen (DE); Johannes Bette, Leonberg (DE); David Minzenmay, Stuttgart (DE)

(73) Assignee: KARDION GMBH, Stuttgart (DE)

( * ) Notice: Subject to any disclaimer, the term of this patent is extended or adjusted under 35 U.S.C. 154(b) by 0 days.

(21) Appl. No.: 17/258,853

(22) PCT Filed: Jul. 9, 2019

(86) PCT No.: PCT/EP2019/068428
§ 371 (c)(1),
(2) Date: Jul. 27, 2021

(87) PCT Pub. No.: WO2020/011795
PCT Pub. Date: Jan. 16, 2020

(65) Prior Publication Data
US 2021/0379358 A1    Dec. 9, 2021

(51) Int. Cl.
*F04D 13/02* (2006.01)
*A61M 60/804* (2021.01)
(Continued)

(52) U.S. Cl.
CPC ......... *F04D 13/024* (2013.01); *A61M 60/174* (2021.01); *A61M 60/237* (2021.01);
(Continued)

(58) Field of Classification Search
CPC .............. A61M 60/419; A61M 60/174; A61M 60/237; A61M 60/408; A61M 60/804;
(Continued)

(56) References Cited

U.S. PATENT DOCUMENTS 2,254,698 A    9/1941   Hansen, Jr.
3,085,407 A    4/1963   Tomlinson
(Continued)

FOREIGN PATENT DOCUMENTS

AU    2002308409    12/2005
AU    2012261669    1/2013
(Continued)

OTHER PUBLICATIONS

International Search Report and Written Opinion received in PCT Application No. PCT/EP2019/068428, dated Oct. 14, 2019 in 13 pages.

(Continued)

*Primary Examiner* — Kenneth J Hansen
(74) *Attorney, Agent, or Firm* — Knobbe, Martens, Olson & Bear LLP

(57) ABSTRACT

An impeller (1) for an implantable vascular support system (2) is provided. The impeller includes an impeller body (3) having a first longitudinal portion (4) and a second longitudinal portion (5) forming a first inner rotor (12) having at least one magnet encapsulated in the second longitudinal portion (5). At least one blade (6) formed in the first longitudinal portion (4) is configured to axially convey a fluid upon rotation. A second outer rotor (13) extends axially and includes at least one magnet. The first rotor (12) and the second rotor (13) form a magnetic coupling (14). The magnets of the first and second rotor being arranged to partially axially overlap with an axial offset and are entirely radially offset.

23 Claims, 5 Drawing Sheets

(51) Int. Cl.
    *A61M 60/237*     (2021.01)
    *A61M 60/419*     (2021.01)
    *A61M 60/408*     (2021.01)
    *A61M 60/174*     (2021.01)
    *F04D 3/02*     (2006.01)
    *F04D 29/18*     (2006.01)
    *F04D 29/20*     (2006.01)
    *F04D 29/60*     (2006.01)
    *A61M 60/416*     (2021.01)
    *A61M 60/82*     (2021.01)
    *A61M 60/857*     (2021.01)

(52) U.S. Cl.
    CPC ........ *A61M 60/408* (2021.01); *A61M 60/416* (2021.01); *A61M 60/419* (2021.01); *A61M 60/804* (2021.01); *A61M 60/82* (2021.01); *A61M 60/857* (2021.01); *F04D 3/02* (2013.01); *F04D 29/181* (2013.01); *F04D 29/20* (2013.01); *F04D 29/60* (2013.01); *A61M 2207/00* (2013.01)

(58) Field of Classification Search
    CPC ............ A61M 2207/00; A61M 60/135; A61M 60/205; F04D 3/02; F04D 29/181; F04D 29/20; F04D 29/60; F04D 13/024
See application file for complete search history.

(56) References Cited

U.S. PATENT DOCUMENTS

| | | | |
|---|---|---|---|
| 3,505,987 A | 4/1970 | Heilman | |
| 3,568,659 A | 3/1971 | Karnegis | |
| 3,614,181 A | 10/1971 | Meeks | |
| 3,747,998 A | 7/1973 | Klein et al. | |
| 3,807,813 A | 4/1974 | Milligan | |
| 3,995,617 A | 12/1976 | Watkins et al. | |
| 4,115,040 A | 9/1978 | Knorr | |
| 4,471,252 A | 9/1984 | West | |
| 4,625,712 A | 12/1986 | Wampler | |
| 4,643,641 A | 2/1987 | Clausen et al. | |
| 4,753,221 A | 6/1988 | Kensey et al. | |
| 4,779,614 A | 10/1988 | Moise | |
| 4,785,795 A | 11/1988 | Singh et al. | |
| 4,817,586 A | 4/1989 | Wampler | |
| 4,846,152 A | 7/1989 | Wampler et al. | |
| 4,888,011 A | 12/1989 | Kung et al. | |
| 4,895,557 A | 1/1990 | Moise et al. | |
| 4,896,754 A | 1/1990 | Carlson et al. | |
| 4,902,272 A | 2/1990 | Milder et al. | |
| 4,908,012 A | 3/1990 | Moise et al. | |
| 4,927,407 A | 5/1990 | Dorman | |
| 4,943,275 A | 7/1990 | Stricker | |
| 4,944,722 A | 7/1990 | Carriker et al. | |
| 4,968,300 A | 11/1990 | Moutafis et al. | |
| 4,985,014 A | 1/1991 | Orejola | |
| 5,044,897 A | 9/1991 | Dorman | |
| 5,061,256 A | 10/1991 | Wampler | |
| 5,089,016 A | 2/1992 | Millner et al. | |
| 5,090,957 A | 2/1992 | Moutafis et al. | |
| 5,112,292 A | 5/1992 | Hwang et al. | |
| 5,112,349 A | 5/1992 | Summers et al. | |
| 5,116,305 A | 5/1992 | Milder et al. | |
| 5,195,877 A | 3/1993 | Kletschka | |
| 5,297,940 A * | 3/1994 | Buse .................... | F04D 13/024 417/423.11 |
| 5,313,765 A | 5/1994 | Martin | |
| 5,344,443 A | 9/1994 | Palma et al. | |
| 5,354,271 A | 10/1994 | Voda | |
| 5,399,145 A | 3/1995 | Ito et al. | |
| 5,405,383 A | 4/1995 | Barr | |
| 5,443,503 A | 8/1995 | Yamane | |
| 5,456,715 A | 10/1995 | Liotta | |
| 5,527,159 A | 6/1996 | Bozeman, Jr. et al. | |
| 5,599,173 A | 2/1997 | Chen et al. | |
| 5,613,935 A | 3/1997 | Jarvik | |
| 5,695,471 A | 12/1997 | Wampler | |
| 5,746,709 A | 5/1998 | Rom et al. | |
| 5,749,855 A | 5/1998 | Reitan | |
| 5,766,207 A | 6/1998 | Potter et al. | |
| 5,831,365 A | 11/1998 | Keim et al. | |
| 5,888,241 A | 3/1999 | Jarvik | |
| 5,888,242 A | 3/1999 | Antaki et al. | |
| 5,904,646 A | 5/1999 | Jarvik | |
| 5,911,685 A | 6/1999 | Siess et al. | |
| 5,921,913 A * | 7/1999 | Siess .................... | H02K 49/104 600/16 |
| 5,964,694 A | 10/1999 | Siess et al. | |
| 6,001,056 A | 12/1999 | Jassawalla et al. | |
| 6,007,478 A | 12/1999 | Siess et al. | |
| 6,018,208 A | 1/2000 | Maher et al. | |
| 6,050,975 A | 4/2000 | Poirier | |
| 6,071,093 A | 6/2000 | Hart | |
| 6,116,862 A * | 9/2000 | Rau .................... | A61M 60/165 417/319 |
| 6,123,659 A | 9/2000 | le Blanc et al. | |
| 6,135,710 A * | 10/2000 | Araki .................. | A61M 60/419 415/206 |
| 6,149,405 A | 11/2000 | Abe et al. | |
| 6,155,969 A * | 12/2000 | Schima ............... | F16C 32/0423 600/16 |
| 6,158,984 A | 12/2000 | Cao et al. | |
| 6,161,838 A | 12/2000 | Balsells | |
| 6,176,848 B1 * | 1/2001 | Rau .................... | A61M 60/419 604/264 |
| 6,186,665 B1 | 2/2001 | Maher et al. | |
| 6,210,318 B1 | 4/2001 | Lederman | |
| 6,217,541 B1 | 4/2001 | Yu | |
| 6,220,832 B1 | 4/2001 | Schob | |
| 6,227,820 B1 | 5/2001 | Jarvik | |
| 6,245,007 B1 | 6/2001 | Bedingham et al. | |
| 6,254,359 B1 | 7/2001 | Aber | |
| 6,264,205 B1 | 7/2001 | Balsells | |
| 6,264,601 B1 | 7/2001 | Jassawalla et al. | |
| 6,264,645 B1 | 7/2001 | Jonkman | |
| 6,293,752 B1 | 9/2001 | Clague et al. | |
| 6,351,048 B1 | 2/2002 | Schob et al. | |
| 6,361,292 B1 | 3/2002 | Chang et al. | |
| 6,432,136 B1 | 8/2002 | Weiss et al. | |
| 6,445,956 B1 | 9/2002 | Laird et al. | |
| 6,447,266 B2 | 9/2002 | Antaki et al. | |
| 6,527,698 B1 | 3/2003 | Kung et al. | |
| 6,530,876 B1 | 3/2003 | Spence | |
| 6,533,716 B1 | 3/2003 | Schmitz-Rode et al. | |
| 6,540,658 B1 | 4/2003 | Fasciano et al. | |
| 6,544,216 B1 | 4/2003 | Sammler et al. | |
| 6,579,257 B1 | 6/2003 | Elgas et al. | |
| 6,592,620 B1 | 7/2003 | Lancisi et al. | |
| 6,595,743 B1 | 7/2003 | Kazatchkov et al. | |
| 6,623,475 B1 | 9/2003 | Siess | |
| 6,719,791 B1 | 4/2004 | Nüsser et al. | |
| 6,794,789 B2 | 9/2004 | Siess et al. | |
| 6,841,910 B2 | 1/2005 | Gery | |
| 6,879,126 B2 | 4/2005 | Paden et al. | |
| 6,912,423 B2 | 6/2005 | Ley et al. | |
| 6,942,611 B2 | 9/2005 | Siess | |
| 6,949,066 B2 | 9/2005 | Bearnson et al. | |
| 6,969,345 B2 | 11/2005 | Jassawalla et al. | |
| 7,027,875 B2 | 4/2006 | Siess et al. | |
| 7,011,620 B1 | 5/2006 | Siess | |
| 7,070,398 B2 | 7/2006 | Olsen et al. | |
| 7,070,555 B2 | 7/2006 | Siess | |
| 7,083,588 B1 | 8/2006 | Shmulewitz et al. | |
| 7,144,364 B2 | 12/2006 | Barbut et al. | |
| 7,160,243 B2 | 1/2007 | Medvedev | |
| 7,238,151 B2 | 7/2007 | Frazier | |
| 7,241,257 B1 | 7/2007 | Ainsworth et al. | |
| 7,264,606 B2 | 9/2007 | Jarvik et al. | |
| 7,462,019 B1 | 12/2008 | Allarie et al. | |
| 7,479,102 B2 | 1/2009 | Jarvik | |
| 7,502,648 B2 | 3/2009 | Okubo et al. | |
| 7,699,586 B2 | 4/2010 | LaRose et al. | |
| 7,736,296 B2 | 6/2010 | Siess et al. | |

(56) References Cited

U.S. PATENT DOCUMENTS

| | | |
|---|---|---|
| 7,762,941 B2 | 7/2010 | Jarvik |
| 7,798,952 B2 | 9/2010 | Tansley et al. |
| 7,841,976 B2 | 11/2010 | McBride et al. |
| 7,850,593 B2 | 12/2010 | Vincent et al. |
| 7,878,967 B1 | 2/2011 | Khanal |
| 7,934,909 B2 | 2/2011 | Jenson |
| 7,914,436 B1 | 3/2011 | Kung |
| 7,959,551 B2 | 6/2011 | Jarvik |
| 7,963,905 B2 | 6/2011 | Salmonsen et al. |
| 7,972,122 B2 | 7/2011 | LaRose et al. |
| 7,998,190 B2 | 8/2011 | Gharib et al. |
| 8,007,254 B2 | 8/2011 | LaRose et al. |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,114,008 B2* | 2/2012 | Hidaka ............... F04D 29/047 600/16 |
| 8,123,669 B2 | 2/2012 | Siess et al. |
| RE43,299 E | 4/2012 | Siess |
| 8,152,845 B2 | 4/2012 | Bourque |
| 8,177,703 B2 | 5/2012 | Smith et al. |
| 8,216,122 B2 | 7/2012 | Kung |
| 8,371,997 B2 | 2/2013 | Shifflette |
| 8,376,926 B2 | 2/2013 | Benkowsi et al. |
| 8,382,695 B1 | 2/2013 | Patel |
| 8,388,565 B2 | 3/2013 | Shifflette |
| 8,419,609 B2 | 4/2013 | Shambaugh, Jr. et al. |
| 8,449,443 B2 | 5/2013 | Rodefeld et al. |
| 8,480,555 B2 | 7/2013 | Kung |
| 8,485,961 B2 | 7/2013 | Campbell et al. |
| 8,512,012 B2* | 8/2013 | Akdis ............... A61M 60/82 417/423.12 |
| 8,535,211 B2 | 9/2013 | Campbell et al. |
| 8,545,380 B2 | 10/2013 | Farnan et al. |
| 8,562,508 B2 | 10/2013 | Dague et al. |
| 8,585,572 B2 | 11/2013 | Mehmanesh |
| 8,591,393 B2 | 11/2013 | Walters et al. |
| 8,591,538 B2 | 11/2013 | Gellman |
| 8,591,539 B2 | 11/2013 | Gellman |
| 8,597,170 B2 | 12/2013 | Walters et al. |
| 8,617,239 B2 | 12/2013 | Reitan |
| 8,622,949 B2 | 1/2014 | Zafirelis et al. |
| 8,641,594 B2 | 2/2014 | LaRose et al. |
| 8,657,875 B2 | 2/2014 | Kung et al. |
| 8,668,473 B2 | 3/2014 | LaRose et al. |
| 8,684,362 B2 | 4/2014 | Balsells et al. |
| 8,684,904 B2 | 4/2014 | Campbell et al. |
| 8,690,749 B1 | 4/2014 | Nunez |
| 8,721,517 B2 | 5/2014 | Zeng et al. |
| 8,727,959 B2 | 5/2014 | Reitan et al. |
| 8,731,664 B2 | 5/2014 | Foster et al. |
| 8,734,331 B2 | 5/2014 | Evans et al. |
| 8,790,236 B2 | 7/2014 | LaRose et al. |
| 8,814,933 B2 | 8/2014 | Siess |
| 8,864,642 B2 | 10/2014 | Scheckel |
| 8,864,643 B2 | 10/2014 | Reichenbach et al. |
| 8,864,644 B2 | 10/2014 | Yomtov |
| 8,882,477 B2 | 11/2014 | Fritz, IV et al. |
| 8,888,728 B2 | 11/2014 | Aboul-Hosn et al. |
| 8,894,387 B2 | 11/2014 | White |
| 8,897,873 B2 | 11/2014 | Schima et al. |
| 8,900,060 B2 | 12/2014 | Liebing |
| 8,900,115 B2 | 12/2014 | Bolling et al. |
| 8,932,246 B2 | 1/2015 | Ferrari |
| 8,992,406 B2 | 3/2015 | Corbett |
| 8,992,407 B2 | 3/2015 | Smith et al. |
| 9,028,216 B2 | 5/2015 | Schumacher et al. |
| 9,028,392 B2 | 5/2015 | Shifflette |
| 9,033,863 B2 | 5/2015 | Jarvik |
| 9,091,271 B2 | 7/2015 | Bourque |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,192,705 B2 | 11/2015 | Yanai et al. |
| 9,199,020 B2 | 12/2015 | Siess |
| 9,265,870 B2 | 2/2016 | Reichenbach et al. |
| 9,297,735 B2 | 3/2016 | Graichen et al. |
| 9,327,068 B2 | 5/2016 | Aboul-Hosn et al. |
| 9,339,598 B2 | 5/2016 | LaRose et al. |
| 9,345,824 B2 | 5/2016 | Mohl et al. |
| 9,370,613 B2 | 6/2016 | Hsu et al. |
| 9,371,826 B2 | 6/2016 | Yanai et al. |
| 9,381,286 B2 | 7/2016 | Spence et al. |
| 9,421,311 B2 | 8/2016 | Tanner et al. |
| 9,433,713 B2 | 9/2016 | Corbett et al. |
| 9,440,013 B2 | 9/2016 | Dowling et al. |
| 9,486,566 B2 | 11/2016 | Siess |
| 9,492,601 B2 | 11/2016 | Casas et al. |
| 9,533,084 B2 | 1/2017 | Siess et al. |
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,579,433 B2 | 2/2017 | LaRose et al. |
| 9,585,991 B2 | 3/2017 | Spence |
| 9,592,397 B2 | 3/2017 | Hansen et al. |
| 9,616,157 B2* | 4/2017 | Akdis ............... F04D 29/0473 |
| 9,623,162 B2 | 4/2017 | Graham et al. |
| 9,623,163 B1 | 4/2017 | Fischi |
| 9,636,442 B2 | 5/2017 | Karmon et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,731,058 B2 | 8/2017 | Siebenhaar et al. |
| 9,737,652 B2 | 8/2017 | LaRose et al. |
| 9,759,222 B2 | 9/2017 | Zimmermann et al. |
| 9,770,543 B2 | 9/2017 | Tanner et al. |
| 9,789,238 B2 | 10/2017 | Aboul-Hosn et al. |
| 9,801,990 B2 | 10/2017 | Lynch |
| 9,814,813 B2 | 11/2017 | Corbett |
| 9,821,100 B2 | 11/2017 | Corbett et al. |
| 9,833,550 B2 | 12/2017 | Siess |
| 9,849,223 B2 | 12/2017 | LaRose |
| 9,878,087 B2 | 1/2018 | Richardson et al. |
| 9,907,890 B2 | 3/2018 | Muller |
| 9,919,087 B2 | 3/2018 | Pfeffer et al. |
| 9,950,101 B2 | 4/2018 | Smith et al. |
| 9,968,719 B2 | 5/2018 | Colella |
| 9,999,714 B2 | 6/2018 | Spanier et al. |
| 10,029,037 B2 | 7/2018 | Muller et al. |
| 10,123,875 B2 | 11/2018 | Wildhirt et al. |
| 10,124,102 B2 | 11/2018 | Bulent et al. |
| 10,179,197 B2 | 1/2019 | Kaiser et al. |
| 10,201,645 B2 | 2/2019 | Muller |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,985 B2 | 4/2019 | Larose et al. |
| 10,251,986 B2 | 4/2019 | Larose et al. |
| 10,279,093 B2 | 5/2019 | Reichenbach et al. |
| 10,293,090 B2 | 5/2019 | Bonde et al. |
| 10,300,249 B2 | 5/2019 | Tao et al. |
| 10,322,217 B2 | 6/2019 | Spence |
| 10,342,906 B2 | 7/2019 | D'Ambrosio et al. |
| 10,357,598 B2 | 7/2019 | Aboul-Hosn et al. |
| 10,371,150 B2 | 8/2019 | Wu et al. |
| 10,376,162 B2 | 8/2019 | Edelman et al. |
| 10,420,869 B2 | 9/2019 | Cornen |
| 10,434,232 B2 | 10/2019 | Wu et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,512,537 B2 | 12/2019 | Corbett |
| 10,525,178 B2 | 1/2020 | Zeng |
| 10,537,670 B2* | 1/2020 | Tuseth ............... A61M 60/857 |
| 10,537,672 B2 | 1/2020 | Tuseth et al. |
| 10,557,475 B2 | 2/2020 | Roehn |

(56) References Cited

U.S. PATENT DOCUMENTS

| | | |
|---|---|---|
| 10,561,771 B2 | 2/2020 | Heilman et al. |
| 10,561,772 B2 | 2/2020 | Schumacher |
| 10,576,191 B2 | 3/2020 | LaRose |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |
| 10,617,808 B2 | 4/2020 | Hastie et al. |
| 10,632,241 B2 | 4/2020 | Schenck et al. |
| 10,660,998 B2 | 5/2020 | Hodges |
| 10,662,967 B2 | 5/2020 | Scheckel |
| 10,668,195 B2 | 6/2020 | Flores |
| 10,669,855 B2 | 6/2020 | Toellner et al. |
| 10,857,273 B2 | 12/2020 | Hodges et al. |
| 11,033,729 B2 | 6/2021 | Scheckel et al. |
| 11,045,638 B2 | 6/2021 | Keenan et al. |
| 11,058,863 B2 | 7/2021 | Demou |
| 11,058,865 B2 | 7/2021 | Fitzgerald et al. |
| 11,065,434 B2 | 7/2021 | Egler et al. |
| 11,092,158 B2 | 8/2021 | Siess et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,978 B2 | 9/2021 | Pfeffer et al. |
| 11,141,579 B2 | 10/2021 | Steingraber |
| 11,160,970 B2 | 11/2021 | Muller et al. |
| 11,167,124 B2 | 11/2021 | Pfeffer et al. |
| 11,173,297 B2 | 11/2021 | Muller |
| 11,179,557 B2 | 11/2021 | Georges et al. |
| 11,185,678 B2 | 11/2021 | Smith et al. |
| 11,185,680 B2 | 11/2021 | Tuval et al. |
| 11,191,944 B2 | 12/2021 | Tuval et al. |
| 11,197,989 B2 | 12/2021 | Arslan et al. |
| 11,202,901 B2 | 12/2021 | Barry |
| 11,219,756 B2 | 1/2022 | Tanner et al. |
| 11,229,786 B2 | 1/2022 | Zeng et al. |
| 11,235,138 B2 | 2/2022 | Gross-Hardt et al. |
| 11,235,140 B2 | 2/2022 | Siess et al. |
| 11,241,568 B2 | 2/2022 | Keenan et al. |
| 11,241,569 B2 | 2/2022 | Delgado, III |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,291,824 B2 | 4/2022 | Schwammenthal et al. |
| 11,291,825 B2 | 4/2022 | Tuval et al. |
| 11,291,826 B2 | 4/2022 | Tuval et al. |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,305,103 B2 | 4/2022 | Larose et al. |
| 11,305,105 B2 | 4/2022 | Corbett et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| D951,435 S | 5/2022 | Motomura et al. |
| 11,318,295 B2 | 5/2022 | Reyes et al. |
| 11,324,940 B2 | 5/2022 | Earles et al. |
| 11,324,941 B2 | 5/2022 | Xu et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,359 B2 | 6/2022 | Clifton et al. |
| 11,357,967 B2 | 6/2022 | Zeng et al. |
| 11,364,373 B2 | 6/2022 | Corbett et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,389,639 B2 | 7/2022 | Casas |
| 11,389,641 B2 | 7/2022 | Nguyen et al. |
| 11,413,443 B2 | 8/2022 | Hodges et al. |
| 11,413,446 B2 | 8/2022 | Siess et al. |
| 11,415,150 B2 | 8/2022 | Richert et al. |
| 11,428,236 B2 | 8/2022 | McBride et al. |
| 11,434,921 B2 | 9/2022 | McBride et al. |
| 11,446,481 B2 | 9/2022 | Wolman et al. |
| 11,446,482 B2 | 9/2022 | Kirchhoff et al. |
| 11,452,859 B2 | 9/2022 | Earles et al. |
| 11,460,030 B2 | 10/2022 | Shambaugh et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,491,320 B2 | 11/2022 | Siess |
| 11,491,322 B2 | 11/2022 | Muller et al. |
| 11,497,896 B2 | 11/2022 | Tanner et al. |
| 11,497,906 B2 | 11/2022 | Grace et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,740 B2 | 12/2022 | Agarwal et al. |
| 11,524,165 B2 | 12/2022 | Tan et al. |
| 11,529,062 B2 | 12/2022 | Moyer et al. |
| 11,534,596 B2 | 12/2022 | Schafir et al. |
| 11,565,103 B2 | 1/2023 | Farago et al. |
| 11,569,015 B2 | 1/2023 | Mourran et al. |
| 11,577,067 B2 | 2/2023 | Breidall et al. |
| 11,577,068 B2 | 2/2023 | Spence et al. |
| 2001/0009645 A1 | 7/2001 | Noda |
| 2001/0041934 A1 | 11/2001 | Yamazaki et al. |
| 2002/0147495 A1 | 10/2002 | Petroff |
| 2002/0153664 A1 | 10/2002 | Schroeder |
| 2003/0111800 A1 | 6/2003 | Kreutzer |
| 2003/0139643 A1 | 7/2003 | Smith et al. |
| 2003/0191357 A1 | 10/2003 | Frazier |
| 2004/0066107 A1 | 4/2004 | Gery |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0019167 A1 | 1/2005 | Nusser et al. |
| 2005/0085683 A1 | 4/2005 | Bolling et al. |
| 2005/0220636 A1 | 10/2005 | Henein et al. |
| 2006/0030809 A1 | 2/2006 | Barzilay et al. |
| 2006/0062672 A1 | 3/2006 | McBride et al. |
| 2006/0155158 A1 | 7/2006 | Aboul-Hosn |
| 2006/0224110 A1 | 10/2006 | Scott et al. |
| 2006/0276682 A1 | 12/2006 | Bolling et al. |
| 2007/0142696 A1 | 6/2007 | Crosby et al. |
| 2008/0015517 A1 | 1/2008 | Geistert et al. |
| 2008/0058925 A1 | 3/2008 | Cohen |
| 2008/0086027 A1 | 4/2008 | Siess et al. |
| 2008/0262289 A1 | 10/2008 | Goldowsky |
| 2008/0292478 A1 | 11/2008 | Baykut et al. |
| 2009/0004037 A1 | 1/2009 | Ito |
| 2009/0112312 A1 | 4/2009 | Larose et al. |
| 2009/0138080 A1 | 5/2009 | Siess et al. |

(56) References Cited

U.S. PATENT DOCUMENTS

| | | |
|---|---|---|
| 2009/0203957 A1 | 8/2009 | LaRose et al. |
| 2009/0204205 A1 | 8/2009 | Larose et al. |
| 2010/0041939 A1 | 2/2010 | Siess |
| 2010/0082099 A1 | 4/2010 | Vodermayer et al. |
| 2010/0191035 A1 | 7/2010 | Kang et al. |
| 2011/0184224 A1 | 7/2011 | Garrigue |
| 2011/0230821 A1 | 9/2011 | Babic |
| 2011/0237863 A1 | 9/2011 | Ricci et al. |
| 2012/0088954 A1 | 4/2012 | Foster |
| 2012/0093628 A1 | 4/2012 | Liebing |
| 2012/0134793 A1 | 5/2012 | Wu et al. |
| 2012/0172655 A1 | 7/2012 | Campbell et al. |
| 2012/0178986 A1 | 7/2012 | Campbell et al. |
| 2012/0283506 A1 | 11/2012 | Meister et al. |
| 2012/0310036 A1 | 12/2012 | Peters et al. |
| 2013/0209292 A1 | 8/2013 | Baykut et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303832 A1 | 11/2013 | Wampler |
| 2013/0330219 A1 | 12/2013 | LaRose et al. |
| 2014/0005467 A1 | 1/2014 | Farnan et al. |
| 2014/0051908 A1 | 2/2014 | Khanal et al. |
| 2014/0079557 A1 | 3/2014 | LaRose et al. |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0275721 A1 | 9/2014 | Yanai et al. |
| 2014/0330069 A1 | 11/2014 | Hastings et al. |
| 2014/0341726 A1 | 11/2014 | Wu et al. |
| 2015/0031936 A1 | 1/2015 | LaRose et al. |
| 2015/0051438 A1 | 2/2015 | Taskin |
| 2015/0099923 A1 | 4/2015 | Magovern et al. |
| 2015/0190092 A1 | 7/2015 | Mori |
| 2015/0290372 A1 | 10/2015 | Muller et al. |
| 2015/0290373 A1 | 10/2015 | Rudser et al. |
| 2015/0306291 A1 | 10/2015 | Bonde et al. |
| 2016/0008531 A1 | 1/2016 | Wang et al. |
| 2016/0038663 A1 | 2/2016 | Taskin et al. |
| 2016/0045654 A1 | 2/2016 | Connor |
| 2016/0144089 A1 | 5/2016 | Woo et al. |
| 2016/0144166 A1 | 5/2016 | Decré et al. |
| 2016/0166747 A1 | 6/2016 | Frazier et al. |
| 2016/0213828 A1 | 7/2016 | Sievers |
| 2016/0223086 A1 | 8/2016 | Balsells et al. |
| 2016/0279311 A1 | 9/2016 | Cecere et al. |
| 2016/0367739 A1 | 12/2016 | Wiesener et al. |
| 2016/0375187 A1 | 12/2016 | Lee et al. |
| 2017/0021069 A1 | 1/2017 | Hodges |
| 2017/0021074 A1 | 1/2017 | Opfermann et al. |
| 2017/0035952 A1 | 2/2017 | Muller |
| 2017/0049947 A1 | 2/2017 | Corbett et al. |
| 2017/0080136 A1 | 3/2017 | Janeczek et al. |
| 2017/0087286 A1 | 3/2017 | Spanier et al. |
| 2017/0087288 A1 | 3/2017 | Groß-HardtTim et al. |
| 2017/0128644 A1 | 5/2017 | Foster |
| 2017/0136225 A1 | 5/2017 | Siess et al. |
| 2017/0143952 A1 | 5/2017 | Siess et al. |
| 2017/0157309 A1 | 6/2017 | Begg et al. |
| 2017/0209633 A1 | 7/2017 | Cohen |
| 2017/0274128 A1 | 9/2017 | Tamburino et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0099076 A1 | 4/2018 | LaRose |
| 2018/0110907 A1 | 4/2018 | Keenan et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0207336 A1 | 7/2018 | Solem |
| 2018/0221551 A1 | 8/2018 | Tanner et al. |
| 2018/0221553 A1 | 8/2018 | Taskin |
| 2018/0228950 A1 | 8/2018 | Janeczek et al. |
| 2018/0228953 A1 | 8/2018 | Siess et al. |
| 2018/0243004 A1 | 8/2018 | von Segesser et al. |
| 2018/0250456 A1 | 9/2018 | Nitzan et al. |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0311423 A1 | 11/2018 | Zeng et al. |
| 2018/0318483 A1 | 11/2018 | Dague et al. |
| 2018/0318547 A1 | 11/2018 | Yokoyama |
| 2018/0326132 A1 | 11/2018 | Maimon et al. |
| 2018/0335037 A1* | 11/2018 | Shambaugh .......... F04D 29/026 |
| 2018/0345028 A1 | 12/2018 | Aboud et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0004037 A1 | 1/2019 | Zhang et al. |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0076167 A1 | 3/2019 | Fantuzzi et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0223877 A1 | 7/2019 | Nitzen et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0290817 A1 | 9/2019 | Guo et al. |
| 2019/0298902 A1 | 10/2019 | Siess et al. |
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2020/0016309 A1 | 1/2020 | Kallenbach et al. |
| 2020/0023109 A1 | 1/2020 | Epple |
| 2020/0030507 A1 | 1/2020 | Higgins et al. |
| 2020/0030509 A1 | 1/2020 | Siess et al. |
| 2020/0030510 A1 | 1/2020 | Higgins |

(56) References Cited

U.S. PATENT DOCUMENTS

| | | | |
|---|---|---|---|
| 2020/0030511 | A1 | 1/2020 | Higgins |
| 2020/0030512 | A1 | 1/2020 | Higgins et al. |
| 2020/0038567 | A1 | 2/2020 | Siess et al. |
| 2020/0038568 | A1 | 2/2020 | Higgins et al. |
| 2020/0038571 | A1 | 2/2020 | Jahangir |
| 2020/0069857 | A1 | 3/2020 | Schwammenthal et al. |
| 2020/0088207 | A1 | 3/2020 | Schumacher et al. |
| 2020/0114053 | A1 | 4/2020 | Salahieh et al. |
| 2020/0129684 | A1 | 4/2020 | Pfeffer et al. |
| 2020/0139028 | A1 | 5/2020 | Scheckel et al. |
| 2020/0139029 | A1 | 5/2020 | Scheckel et al. |
| 2020/0147283 | A1 | 5/2020 | Tanner et al. |
| 2020/0164125 | A1 | 5/2020 | Muller et al. |
| 2020/0164126 | A1 | 5/2020 | Muller |
| 2020/0350812 | A1 | 11/2020 | Vogt et al. |
| 2021/0052793 | A1 | 2/2021 | Struthers et al. |
| 2021/0236803 | A1 | 8/2021 | Stotz |
| 2021/0268264 | A1 | 9/2021 | Stotz |
| 2021/0290929 | A1 | 9/2021 | Stotz |
| 2021/0290930 | A1 | 9/2021 | Kasel |
| 2021/0290932 | A1 | 9/2021 | Stotz |
| 2021/0290937 | A1 | 9/2021 | Baumbach |
| 2021/0313869 | A1 | 10/2021 | Strasswiemer et al. |
| 2021/0316133 | A1 | 10/2021 | Kassel et al. |
| 2021/0322756 | A1 | 10/2021 | Vollmer et al. |
| 2021/0330958 | A1 | 10/2021 | Stotz et al. |
| 2021/0338999 | A1 | 11/2021 | Stotz et al. |
| 2021/0339004 | A1 | 11/2021 | Schlebusch et al. |
| 2021/0339005 | A1 | 11/2021 | Stotz et al. |
| 2021/0346678 | A1 | 11/2021 | Baumbach et al. |
| 2021/0346680 | A1 | 11/2021 | Vogt et al. |
| 2021/0379352 | A1 | 12/2021 | Schlebusch et al. |
| 2021/0379355 | A1 | 12/2021 | Schuelke et al. |
| 2021/0384812 | A1 | 12/2021 | Vollmer et al. |
| 2022/0008714 | A1 | 1/2022 | Stotz |
| 2022/0016411 | A1 | 1/2022 | Winterwerber |
| 2022/0072296 | A1 | 3/2022 | Mori |
| 2022/0072297 | A1 | 3/2022 | Tuval et al. |
| 2022/0080178 | A1 | 3/2022 | Salahieh et al. |
| 2022/0080180 | A1 | 3/2022 | Siess et al. |
| 2022/0080182 | A1 | 3/2022 | Earles et al. |
| 2022/0080183 | A1 | 3/2022 | Earles et al. |
| 2022/0080184 | A1 | 3/2022 | Clifton et al. |
| 2022/0080185 | A1 | 3/2022 | Clifton et al. |
| 2022/0105337 | A1 | 4/2022 | Salahieh et al. |
| 2022/0105339 | A1 | 4/2022 | Nix et al. |
| 2022/0126083 | A1 | 4/2022 | Grauwinkel et al. |
| 2022/0161018 | A1 | 5/2022 | Mitze et al. |
| 2022/0161019 | A1 | 5/2022 | Mitze et al. |
| 2022/0161021 | A1 | 5/2022 | Mitze et al. |
| 2022/0241580 | A1 | 8/2022 | Stotz et al. |
| 2022/0407403 | A1 | 12/2022 | Vogt et al. |
| 2023/0001178 | A1 | 1/2023 | Corbett et al. |

FOREIGN PATENT DOCUMENTS

| | | |
|---|---|---|
| AU | 2013203301 | 5/2013 |
| AU | 2013273663 | 1/2014 |
| BR | PI0904483-3 | 7/2011 |
| CA | 2 026 692 | 4/1992 |
| CA | 2 026 693 | 4/1992 |
| CA | 2 796 357 | 10/2011 |
| CN | 1222862 A | 7/1999 |
| CN | 1254598 A | 5/2000 |
| CN | 1376523 A | 10/2002 |
| CN | 2535055 | 2/2003 |
| CN | 1118304 C | 8/2003 |
| CN | 2616217 | 5/2004 |
| CN | 1202871 C | 5/2005 |
| CN | 1833736 A | 9/2006 |
| CN | 200977306 | 11/2007 |
| CN | 101112628 | 1/2008 |
| CN | 201150675 | 11/2008 |
| CN | 201437016 | 4/2010 |
| CN | 201618200 | 11/2010 |
| CN | 201658687 | 12/2010 |
| CN | 201710717 | 1/2011 |
| CN | 201894758 | 7/2011 |
| CN | 102475923 | 5/2012 |
| CN | 102545538 | 7/2012 |
| CN | 202314596 | 7/2012 |
| CN | 102743801 | 10/2012 |
| CN | 103143072 | 6/2013 |
| CN | 103845766 | 6/2014 |
| CN | 103861162 | 6/2014 |
| CN | 203842087 | 9/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 104888293 | 3/2017 |
| CN | 106512117 | 3/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 105498002 | 6/2018 |
| CN | 106310410 | 7/2018 |
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| DE | 1 001 642 | 1/1957 |
| DE | 1 165 144 | 3/1964 |
| DE | 26 24 058 | 12/1977 |
| DE | 3 545 214 | 7/1986 |
| DE | 195 46 336 | 5/1997 |
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 100 59 714 | 5/2002 |
| DE | 101 55 011 | 11/2005 |
| DE | 601 19 592 | 9/2006 |
| DE | 20 2005 020 288 | 6/2007 |
| DE | 10 2008 060 357 | 6/2010 |
| DE | 10 2009 039 658 | 3/2011 |
| DE | 20 2009 018 416 | 8/2011 |
| DE | 10 2012 022 456 | 5/2014 |
| DE | 10 2013 007 562 | 11/2014 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 20 2015 009 422 | 7/2017 |
| DE | 10 2012 207 042 | 9/2017 |
| DE | 10 2016 013 334 | 4/2018 |
| DE | 10 2017 212 193 | 1/2019 |
| DE | 10 2018 207 611 | 11/2019 |
| DE | 10 2018 208 945 | 12/2019 |
| DE | 10 2018 211 327 | 1/2020 |
| DE | 10 2018 212 153 | 1/2020 |
| DE | 10 2018 213 350 | 2/2020 |
| DE | 11 2020 003 063 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 1 013 294 | 6/2000 |
| EP | 1 186 873 | 3/2002 |
| EP | 1 475 880 | 11/2004 |
| EP | 1 169 072 | 5/2005 |

(56) References Cited

FOREIGN PATENT DOCUMENTS

| | | |
|---|---|---|
| EP | 1 176 999 | 7/2005 |
| EP | 1 801 420 | 6/2007 |
| EP | 2 009 233 | 12/2008 |
| EP | 2 098 746 | 9/2009 |
| EP | 2 403 109 | 1/2012 |
| EP | 2 187 807 | 6/2012 |
| EP | 3 326 567 | 10/2014 |
| EP | 1 898 971 | 3/2015 |
| EP | 2 519 273 | 8/2015 |
| EP | 2 438 936 | 10/2015 |
| EP | 2 438 937 | 10/2015 |
| EP | 2 960 515 | 12/2015 |
| EP | 1 996 252 | 5/2016 |
| EP | 2 475 415 | 6/2016 |
| EP | 2 906 265 | 7/2016 |
| EP | 3 069 739 | 9/2016 |
| EP | 3 127 562 | 2/2017 |
| EP | 2 585 129 | 3/2017 |
| EP | 3 143 682 | 3/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 3 205 359 | 8/2018 |
| EP | 3 205 360 | 8/2018 |
| EP | 3 456 367 | 3/2019 |
| EP | 3 542 835 | 9/2019 |
| EP | 3 542 836 | 9/2019 |
| EP | 3 711 785 | 9/2020 |
| EP | 3 711 786 | 9/2020 |
| EP | 3 711 787 | 9/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 2 344 218 | 4/2021 |
| EP | 3 436 104 | 4/2021 |
| EP | 3 749 383 | 4/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 884 968 | 9/2021 |
| EP | 3 884 969 | 9/2021 |
| EP | 3 027 241 | 10/2021 |
| EP | 3 579 904 | 11/2021 |
| EP | 2 628 493 | 12/2021 |
| EP | 3 556 409 | 1/2022 |
| EP | 3 624 868 | 1/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 219 339 | 6/2022 |
| EP | 3 737 310 | 7/2022 |
| EP | 3 899 994 | 8/2022 |
| EP | 3 487 550 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 866 876 | 11/2022 |
| EP | 3 941 546 | 11/2022 |
| EP | 2 892 583 | 1/2023 |
| EP | 3 597 231 | 1/2023 |
| EP | 3 656 292 | 1/2023 |
| EP | 3 768 345 | 1/2023 |
| EP | 3 539 585 | 2/2023 |
| FR | 1458525 | 3/1966 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 545 062 | 6/2017 |
| GB | 2 545 750 | 6/2017 |
| JP | 59-119788 | 8/1984 |
| JP | S61-500059 | 1/1986 |
| JP | S62-113555 | 7/1987 |
| JP | S64-68236 | 3/1989 |
| JP | 2-79738 | 3/1990 |
| JP | H04-176471 | 6/1992 |
| JP | H04-108384 | 9/1992 |
| JP | 2888609 | 5/1999 |
| JP | 2889384 | 5/1999 |
| JP | H11-239617 | 9/1999 |
| JP | 2004-278375 | 10/2004 |
| JP | 2008-511414 | 4/2008 |
| JP | 2008-516654 | 5/2008 |
| JP | 2010-258181 | 11/2010 |
| JP | 2013-013216 | 1/2013 |
| JP | 2014-004303 | 1/2014 |
| JP | 2015-514531 | 5/2015 |
| JP | 2016-002466 | 1/2016 |
| JP | 2016-532500 | 10/2016 |
| JP | 6267625 | 1/2018 |
| JP | 6572056 | 9/2019 |
| JP | 2020-072985 | 5/2020 |
| KR | 10-2011-0098192 | 9/2011 |
| RO | 131676 | 2/2017 |
| RU | 2 051 695 | 1/1996 |
| TW | 374317 | 11/1999 |
| WO | WO 94/009835 | 5/1994 |
| WO | WO 97/037696 | 10/1997 |
| WO | WO 97/039785 | 10/1997 |
| WO | WO 99/049912 | 10/1999 |
| WO | WO 00/033446 | 6/2000 |
| WO | WO 02/022200 | 3/2002 |
| WO | WO 02/070039 | 9/2002 |
| WO | WO 03/075981 | 9/2003 |
| WO | WO 03/103745 | 12/2003 |
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO 2008/081783 | 7/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2011/003043 | 1/2011 |
| WO | WO 2011/081626 | 7/2011 |
| WO | WO 2012/047540 | 4/2012 |
| WO | WO 2012/112129 | 8/2012 |

(56) References Cited

FOREIGN PATENT DOCUMENTS

| | | |
|---|---|---|
| WO | WO 2013/037380 | 3/2013 |
| WO | WO 2013/120957 | 8/2013 |
| WO | WO 2013/167432 | 11/2013 |
| WO | WO 2013/173239 | 11/2013 |
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/172173 | 11/2015 |
| WO | WO 2015/175718 | 11/2015 |
| WO | WO 2016/028644 | 2/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/053988 | 3/2017 |
| WO | WO 2017/060257 | 4/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/205909 | 12/2017 |
| WO | WO 2018/088939 | 3/2018 |
| WO | WO 2018/109038 | 6/2018 |
| WO | WO 2018/139508 | 8/2018 |
| WO | WO 2018/197306 | 11/2018 |
| WO | WO 2019/034670 | 2/2019 |
| WO | WO 2019/035804 | 2/2019 |
| WO | WO 2019/038343 | 2/2019 |
| WO | WO 2019/057636 | 3/2019 |
| WO | WO 2019/078723 | 4/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/180104 | 9/2019 |
| WO | WO 2019/180179 | 9/2019 |
| WO | WO 2019/180181 | 9/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/132211 | 6/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2023/278599 | 1/2023 |
| WO | WO 2023/014742 | 2/2023 |
| WO | WO 2023/049813 | 3/2023 |
| WO | WO 2023/076869 | 5/2023 |

OTHER PUBLICATIONS

International Preliminary Report on Patentability and Written Opinion received in PCT Application No. PCT/EP2019/068428, dated Jan. 21, 2021 in 8 pages.
"ABMD—Taking a Closer Look at Impella ECP as the Pivotal Trial Gets Underway", Guggenheim, Press Release, Mar. 29, 2022, pp. 4.
Vollkron et al., "Advanced Suction Detection for an Axial Flow Pump", Artificial Organs, 2006, vol. 30, No. 9, pp. 665-670.
Vollkron et al., "Development of a Suction Detection System for Axial Blood Pumps", Artificiai Organs, 2004, vol. 28, No. 8, pp. 709-716.

* cited by examiner ately small outer diameter and wall thicknesses, with which the limited installation space in VAD axial flow pumps, which are intended to be implanted inside the aorta, can be used to maximum advantage. In particular the encapsulation of the at least one magnet in the second longitudinal portion contributes to the long-term stability of the system. This advantageously allows the construction of a magnet system which can transmit the required torques and at the same time encapsulates the magnets in the motor and impeller in a biocompatible and long-term stable manner.
IMPELLER FOR AN IMPLANTABLE, VASCULAR SUPPORT SYSTEM

BACKGROUND

Field

The invention relates to an impeller for an implantable vascular support system, an implantable vascular support system, and a method for producing an impeller for an implantable vascular support system. The invention is used in particular in (fully) implanted left ventricular assist devices (LVAD).

Description of the Related Art

Today's LVAD cardiac support systems can generally be differentiated in terms of their position on the heart and their access to the blood stream. Approved long-term support systems are positioned at the apex of the heart (transapically) and bypass the left ventricle by pumping blood from the apex of the heart through a hose directly into the aorta (bypass). Since these systems are not located within the cardiovascular system itself, but are placed outside the heart, the available installation space for the pumps is relatively large. The housings in which the impeller moves are multiple centimeters in size.

A (percutaneous) minimally invasive or (fully) implanted support system in aortic valve position, which is currently used primarily for short-term support (so-called bridge to decision, bridge to transplant), represents another type of access. In this case, the natural aortic valve is used to create a separation between the pump inlet and the pump outlet. The advantage of this arrangement is that the aorta can be used as an access route (transfemoral or transaortic) in the context of a minimally invasive surgical procedure and there is no need for a sternotomy. With this type of support system, the installation space (length and outer diameter) is very limited due to the access route. A disadvantage of small pumps, however, is the comparatively low efficiency and the resulting reduced volume flow.

SUMMARY

The object of the invention is to provide an impeller for an implantable vascular support system and an implantable vascular support system. One object of the invention is in particular to provide an impeller for an implantable vascular support system and a vascular support system which is (fully) implantable in aortic valve position, which is long-term stable and is suitable not only for short-term support of the heart function of a person and whereby the efficiency of the vascular support system is improved.

This object is achieved by the impeller described herein and the implantable vascular support system described herein, as well as the method for producing an impeller housing for an implantable vascular support system described herein.

Advantageous embodiments of the invention are described herein.

Proposed here is an impeller for an implantable vascular support system, at least comprising:
  an impeller body having a first longitudinal portion and a second longitudinal portion,
  at least one blade, which is formed in the first longitudinal portion and is configured to axially convey a fluid with a rotational movement,
  at least one magnet, which is disposed and encapsulated in the second longitudinal portion.

In other words, the solution presented here in particular describes a preferably multipart impeller for a VAD pump having an integrated magnetic coupling. The solution presented here contributes advantageously to providing a long-term stable system for contactless torque transmission in an implantable vascular support system. The allocation of the functions fluid conveyance and torque transmission to different longitudinal portions of the impeller body makes it possible to achieve a particularly advantageous compact design with a comparatively small outer diameter and wall thicknesses, with which the limited installation space in VAD axial flow pumps, which are intended to be implanted inside the aorta, can be used to maximum advantage. In particular the encapsulation of the at least one magnet in the second longitudinal portion contributes to the long-term stability of the system. This advantageously allows the construction of a magnet system which can transmit the required torques and at the same time encapsulates the magnets in the motor and impeller in a biocompatible and long-term stable manner.

The impeller comprises an impeller body having a first longitudinal portion and a second longitudinal portion. In other words, this means in particular that the (elongated and/or hose-like) impeller body can be subdivided into a first longitudinal portion and a second longitudinal portion. In the case of a one-piece impeller body, this subdivision would be discernible only conceptually and/or by a difference in the wall thickness, for example.

In the case of a multipart impeller body, said impeller body could in particular be multipart in that the first longitudinal portion and the second longitudinal portion are separate parts or elements of the impeller body. In other words, in the case of a multipart impeller body, this means in particular that the first longitudinal portion describes a first impeller body element (which can also be described as a blading component) and the second longitudinal portion describes a second impeller body element (which can also be described as a magnet mount). In this case, the first impeller body element and the second impeller body element together form the impeller body. For this purpose, said elements are typically connected to one another (in a material-locking manner); for example, they can be (thermally) joined to one another at their ends, for example brazed or welded.

The impeller body can have the (basic) shape of a (elongated) cylinder, for example. "Elongated" here means in particular that the longitudinal extension is at least twice as large as the (maximum) diameter. The second longitudinal portion of the impeller body preferably has the shape of a (elongated) tube with a circular cross-section. The second impeller body element (if present) can have the shape of a pipe section.

The impeller further comprises at least one blade, which is formed in the first longitudinal portion and is configured to axially convey a fluid with a rotational movement. The blade can be formed in one piece with the first longitudinal portion, for example. The blade can alternatively be (detachably or fixedly) connected to the first longitudinal portion. The blade is preferably thermally joined to the first longitudinal portion. The blade is preferably configured to convey a fluid with a flow direction parallel to the longitudinal axis of the impeller. In other words, this means in particular that the impeller is configured to in particular act as an impeller of an axial flow pump. An axial flow pump is a pump that conveys fluids with a rotational movement axially, i.e.

parallel to the axis of the pump shaft. For this purpose, the blade can be spatially curved.

The impeller further comprises at least one magnet, which is disposed in the second longitudinal portion and encapsulated (with respect to the environment). The (full) encapsulation of the at least one magnet advantageously contributes to the fact that the impeller can be used biocompatibly in the body, because the conveyed blood cannot come into direct contact with the magnet.

In order to transmit a torque radially, a plurality of magnet segments (usually between 4 and 8 magnet segments) having different magnetization directions are preferably used. These magnet segments are preferably disposed to form a pipe section or an annular arrangement of magnets. This pipe section or this arrangement of magnets preferably has a wall thickness of approx. 0.5 mm to 1.5 mm. A plurality of magnetic circuits can furthermore also be constructed in axial direction (e.g. a two-part magnetic coupling). Due to the high coercive field strength, the use of neodymium iron-boron magnets is preferred, but these are generally susceptible to corrosion and are therefore not readily biocompatible. For this reason, the encapsulation of such magnets is particularly advantageous.

The impeller body preferably comprises a magnet mount in the second longitudinal portion or the second longitudinal portion is shaped in the manner of a magnet mount. The magnet mount can be configured to accommodate a magnet assembly. In this context, the magnet assembly comprises at least one magnet and at least one magnetic return.

The magnetic return serves in particular to guide the magnetic field lines, which advantageously allows higher torques to be transmitted. The materials used are, for example, magnetizable, ferrous materials. The magnetic return is preferably configured in the form of a pipe section. This pipe section particularly preferably has a wall thickness of approx. 0.4 mm.

The magnet mount comprises a recess, for example, which can extend into the impeller body in radial direction (radial coupling) or in axial direction (axial coupling). This recess preferably has a rectangular cross-sectional shape.

The recess (the magnet mount) preferably extends radially inward from a jacket surface (cylinder outer surface) of the second longitudinal portion. In this context, it is further preferred for the recess to be delimited (in radial direction) by an inner wall of the impeller body, which in particular at the same time delimits (in radial direction) a space for accommodating an inner rotor or drive rotor that cooperates with the at least one magnet of the impeller.

The recess (of the magnet mount) further preferably extends (axially) from an end face of the second longitudinal portion of the impeller body facing away from the first longitudinal portion in the direction of the first longitudinal portion. In this context, it is further preferred for the recess to be delimited (in radial direction) by an inner surface of the impeller body, which is orthogonal to the longitudinal axis of the impeller body.

The recess is preferably configured and/or dimensioned and shaped such that it can fully accommodate the magnet assembly. In addition, the (only one) opening of the recess is preferably configured such that it can be closed (hermetically) with a cover. The recess and the cover particularly advantageously form a capsule, in which the magnet assembly or the at least one magnet is disposed and encapsulated.

In the second longitudinal portion, the impeller body preferably has a wall thickness that is less than or equal to 2 mm [millimeters], preferably less than or equal to 1.5 mm or even less than or equal to 1 mm. The wall thicknesses are particularly preferred in the range of 0.01 mm to 0.5 mm or even in the range of 0.05 mm to 0.2 mm. The wall with the correspondingly small wall thickness can be the above-described inner wall (e.g. in the case of a radial coupling), for example, or a jacket (e.g. in the case of an axial coupling) of the second longitudinal portion or a wall in the region of the magnet mount. The correspondingly small wall thickness can also pertain to the wall thickness of a cover or a sleeve for encapsulating the magnet. A correspondingly small wall thickness in the second longitudinal portion or in the region of the magnet mount contributes to this particularly advantageously, so that an advantageously high torque can be transmitted for cardiac support even in a small installation space.

According to one advantageous configuration, it is proposed that the impeller body be formed in one piece. In other words, this means in particular that the first longitudinal portion and the second longitudinal portion of the impeller body are formed in one piece (with one another). Preferably, in this context, the impeller body and the at least one blade are also formed in one piece (with one another). A milling process, a casting process or an additive manufacturing process, such as a 3D printing process, for example, can be used for one-piece production.

According to another advantageous configuration, it is proposed that the impeller body be formed in multiple parts. A multipart impeller body is particularly advantageous with respect to the mass moment of inertia of the rotor, the durability of the blades and/or the thrombogenicity of the surfaces. It can furthermore also be advantageous for manufacturing and assembly reasons as well as for cost reasons to construct the impeller in multiple parts.

A multipart impeller represents a particularly advantageous aspect of the solution presented here. This design advantageously allows a clear separation according to function, so that, for example, one part of the impeller is responsible for conveying the fluid (requirements: high degree of precision for the blade geometry, very smooth surfaces), another for transmitting the torque (requirements: hermetic tightness to ingress of fluid, high balancing quality). In the case of multipart production, individual parts/assemblies can particularly advantageously be tested separately prior to final assembly (e.g. for tightness due to the susceptibility of the magnets to corrosion, for functionality of the coupling or for rotational speed stability). Another advantage is the free combinability of the parts (the magnetic coupling remains the same, for example, but there are different blade geometries or materials, e.g. plastic blading for short-term use, titanium or ceramic blading for long-term use).

In this context, the first longitudinal portion and the second longitudinal portion are preferably thermally joined to one another. Said portions are preferably joined to one another at their ends. A welding process or a brazing process can be used for thermal joining. The first longitudinal portion and the second longitudinal portion are preferably connected to one another with a (radially) circumferential weld seam.

Furthermore, for a multipart design, long-term stable joints are particularly advantageous for long-term use and functional integrity. For this purpose, facing end faces of the first and second longitudinal portions can comprise centering elements which enable a thermal joining connection, such as a (radially) circumferential weld seam of particularly high quality.

According to one advantageous configuration, it is proposed that the second longitudinal portion forms a rotor for a magnetic coupling. The second longitudinal portion preferably forms an outer rotor for a magnetic coupling. A torque can thus be transmitted particularly advantageously without contact.

The second longitudinal portion preferably forms a first rotor of a magnetic coupling (which comprises two rotors). The second rotor can be formed with a drive shaft with which (drive) magnets are fixedly connected. The second longitudinal portion can thus represent an output side of a magnetic coupling. The magnetic coupling can be configured as a radial coupling or as an axial coupling. In the case of a radial coupling, the first rotor and the second rotor are disposed one behind the other in radial direction and at least partially overlapping in axial direction. In the case of an axial coupling, the first rotor and the second rotor are disposed one behind the other in axial direction and at least partially overlapping in radial direction.

The impeller or the impeller body is furthermore preferably made of a high-strength and/or biocompatible material. Grade 5 titanium, for example, can be used for this purpose. This results in the significant advantage that the support system can remain implanted for as long as possible. Grade 5 titanium can furthermore advantageously ensure a weldable joint.

According to a further aspect, an implantable vascular support system which comprises a here proposed impeller is proposed as well. The support system typically also comprises an impeller housing in which the impeller is held (in the manner of an impeller).

The vascular support system is preferably a cardiac support system, particularly preferably a ventricular support system. The support system is regularly used to support the conveyance of blood in the circulatory system of humans, e.g. a patient. The support system can be disposed at least partially in a blood vessel. The blood vessel is the aorta, for example, in particular in the case of a left heart support system, or the common trunk (truncus pulmonalis) into the two pulmonary arteries, in particular in the case of a right heart support system. The support system can preferably be disposed at the outlet of the left ventricle of the heart or the left ventricle. The support system can particularly preferably be disposed in aortic valve position. The support system is preferably a left ventricular cardiac support system (LVAD) or a percutaneous, minimally invasive left heart support system. The system is furthermore preferably fully implantable. In other words, this means in particular that the means required for conveying blood, in particular a flow machine (having an impeller and an impeller housing) of the support system, are located entirely within the patient's body (in particular in the heart and/or the aorta) and remain there. However, it is not mandatory that a control device or an evaluation device of the support system also be disposed inside the patient's body. For example, the support system can be implanted such that the control device or evaluation device is disposed on the patient's skin or outside the patient's body and a connection to the flow machine disposed inside the body is established. The support system is particularly preferably configured and/or suited to being disposed at least partially in a ventricle, preferably in the left ventricle of a heart, and/or in an aorta, in particular in aortic valve position.

The support system further preferably comprises a cannula, in particular an inlet cannula, a flow machine, such as a pump (with an impeller), and/or an electric motor. The electric motor is regularly a component of the flow machine. The (inlet) cannula (suction hose) is preferably configured such that, in the implanted state, it can conduct fluid from a (left) ventricle of a heart to the flow machine. The support system is preferably elongated and/or hose-like. The cannula and the flow machine are preferably disposed in the region of opposite ends of the support system.

The support system is in particular configured such that it can be implanted (in a minimally invasive manner) in aortic valve position. For this purpose, the support system preferably has an outer diameter in the range of 4 mm to 10 mm, particularly preferably in the range of 5 mm to 8 mm and/or a (rigid) length in the range of 10 mm to 80 mm, particularly preferably in the range of 20 mm to 50 mm. Such a dimensioning of the support system advantageously allows the support system to be implanted in a minimally invasive manner in aortic valve position while still maintaining good functionality, in particular comparatively high efficiency. In the case of a transfemoral access route, the installation space for the support system (the pump) is very limited because the femoral artery has a relatively small diameter, so the outer diameter of the support system should be as small as possible. The efficiency of an impeller of the pump should nonetheless not become too low. The support system is furthermore pushed around the aortic arch, which can typically describe an arc of >180°. To overcome this anatomical constriction, the overall rigid length of an implant should also be kept as small as possible.

According to a further aspect, a method for producing an impeller for an implantable, vascular support system is proposed as well and at least comprises the following steps:
a) providing an impeller body having a first longitudinal portion and a second longitudinal portion, wherein at least one blade is formed in the first longitudinal portion and configured to axially convey a fluid by means of a rotational movement,
b) providing at least one magnet,
c) disposing and encapsulating the magnet in the second longitudinal portion.

The specified sequence of the method steps a), b) and c) is only an example and can be the result of a regular operating sequence.

According to one advantageous configuration, it is proposed that the impeller body be provided in one piece in Step a). In this context, it is advantageous if the at least one magnet or the one magnet assembly is (initially) disposed in a sleeve and/or (fixedly) connected to said sleeve. The at least one magnet or the magnet assembly can furthermore (then) be pushed onto the second longitudinal portion of the impeller body in and/or with the sleeve. In this context, it is particularly advantageous if the sleeve is configured or shaped such that, in the pushed-on state, it encapsulates the at least one magnet or the magnet assembly in cooperation with the second longitudinal portion. It is furthermore advantageous if the joints between the sleeve and the impeller body (radial and axial) are thermally joined, in particular welded.

During operation, the sleeve serves in particular to encapsulate the non-biocompatible materials (magnets, return). In order to take up as little installation space as possible, it is particularly advantageous if the wall thickness of the sleeve is kept as low as possible. In this context, a preferred wall thickness of the sleeve is approx. 0.1 mm. In particular if the sleeve is to be machined, a biocompatible metal can be used, e. g. Grade 5 titanium. The material in the region between the two magnetic rotors can furthermore also be non-magnetic, e.g. titanium or plastic. This material can be formed in the manner of a so-called split case of a magnetic coupling, for example. This in particular does not (disadvantageously) affect the function of the magnetic coupling.

The joints between the sleeve and the impeller body are advantageously welded hermetically tight. The mentioned assembly steps (pushing on the sleeve with the magnets located therein) result in particular in a radial and an axial weld seam. The magnet system in the impeller is thus advantageously completely encapsulated, but can nonetheless transmit the magnetic forces and with it the torque in a particularly advantageous manner without contact.

According to another advantageous configuration, it is proposed that the impeller body be provided in multiple parts in Step a). A separation (between the first longitudinal portion and the second longitudinal portion) advantageously results in further degrees of freedom also in terms of production. The blading can also be produced in an investment casting process, for example, or via 3D printing. In particular when using hard materials (ceramic or DLC layers), the bearing function can be implemented in the geometry. All in all, a more cost-effective and significantly more flexible production can advantageously be achieved.

In this context (multipart impeller body), the second longitudinal portion is preferably assembled before the second longitudinal portion is connected to the first longitudinal portion. This assembly can, for example, include an insertion of the at least one magnet or a magnet assembly into a magnet mount. This assembly can furthermore (subsequently) include closing the magnet mount with a cover and, if necessary, thermally joining the cover to the second longitudinal portion.

Further preferably, in this context (multipart impeller body), a connection, in particular thermal joining of the first longitudinal portion and the second longitudinal portion, is carried out. It is furthermore preferred that a testing or inspection of the first longitudinal portion and/or the second longitudinal portion (independent of one another), in particular of the joints of the second longitudinal portion, take place (chronologically) before the connection (and after the above-described assembly of the second longitudinal portion). This can include a tightness test of the second longitudinal portion, in particular the magnet mount of the second longitudinal portion. This can alternatively or cumulatively include a test of the second longitudinal portion for tightness of the joints (because of the susceptibility of the magnets to corrosion), for functionality of the coupling and/or for rotational speed stability.

According to one advantageous configuration, it is proposed that a magnet assembly comprising the at least one magnet and a magnetic return be provided in Step b). The magnetic return serves in particular to guide the magnetic field lines, which advantageously allows higher torques to be transmitted. The magnetic return is in particular disposed such that it surrounds the at least one magnet circumferentially.

According to one advantageous configuration, it is proposed that the magnet be encapsulated with a cover in Step c). The cover can be a sleeve, for example, which is configured such that the at least one magnet or the magnet assembly can be pushed onto the second longitudinal portion of the impeller body in and/or with the sleeve. The cover can furthermore be a cover that is configured to close an (radial or axial) opening of a magnet mount. In this context, the cover can be formed with a (thin-walled) pipe section or a (thin-walled) wound (and possibly longitudinally welded) sheet metal, for example.

The details, features and advantageous configurations discussed in connection with the impeller can correspondingly also occur in the support system and/or the method presented here and vice versa. In this respect, reference is made in full to the statements there for a more detailed characterization of the features.

BRIEF DESCRIPTION OF THE DRAWINGS

The solution presented here as well as its technical environment are explained in more detail below with reference to the figures. It is important to note that the invention is not intended to be limited by the design examples shown. In particular, unless explicitly stated otherwise, it is also possible to extract partial aspects of the facts explained in the figures and to combine them with other components and/or insights from other figures and/or the present description.

The figures show schematically.

DETAILED DESCRIPTION

Figure 1:
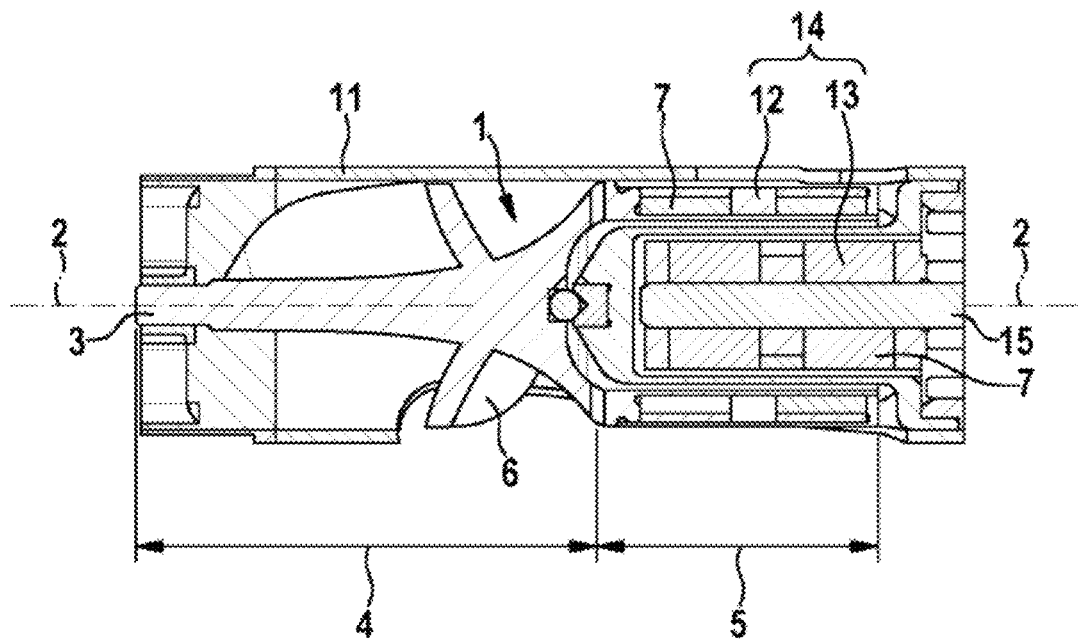
FIG. 1: a here proposed impeller in an impeller housing.

FIG. 1 schematically shows a here proposed impeller 1 in an impeller housing 11. The impeller 1 is suitable for an implantable vascular support system (not shown here, see FIG. 9). The impeller 1 can generally also be used in small axial flow pumps (with impeller), in particular with contactless torque transmission.

The impeller 1 comprises an impeller body 3 which is rotatable about an axis of rotation 2 and has a first longitudinal portion 4 which extends in the direction of the axis of rotation 2 and a second longitudinal portion 5 which extends in the direction of the axis of rotation 2. The impeller 1 further comprises at least one blade 6, which is formed in the first longitudinal portion 4 and is configured to axially convey a fluid in the direction of the axis of rotation 2 with a rotational movement. The impeller 1 also comprises at least one magnet 7, which is disposed and encapsulated in the second longitudinal portion 5.

In FIG. 1, the impeller body 3 is formed in one piece. For this purpose, the first longitudinal portion 4 and the second longitudinal portion 5 of the impeller body 3 are formed in one piece.

FIG. 1 further illustrates that the second longitudinal portion 4 forms a first rotor 12 (outer rotor) for a magnetic coupling 14. The first rotor 12 cooperates (for radial torque transmission) with a second rotor 13 (inner rotor). The second rotor 13 is formed with magnets 7, which are fixedly connected to a drive shaft 15. The first rotor 12 and the second rotor 13 form the magnetic coupling 14. In the embodiment according to FIG. 1, the magnetic coupling 14 is formed in the manner of a radial coupling system.

Figure 2:
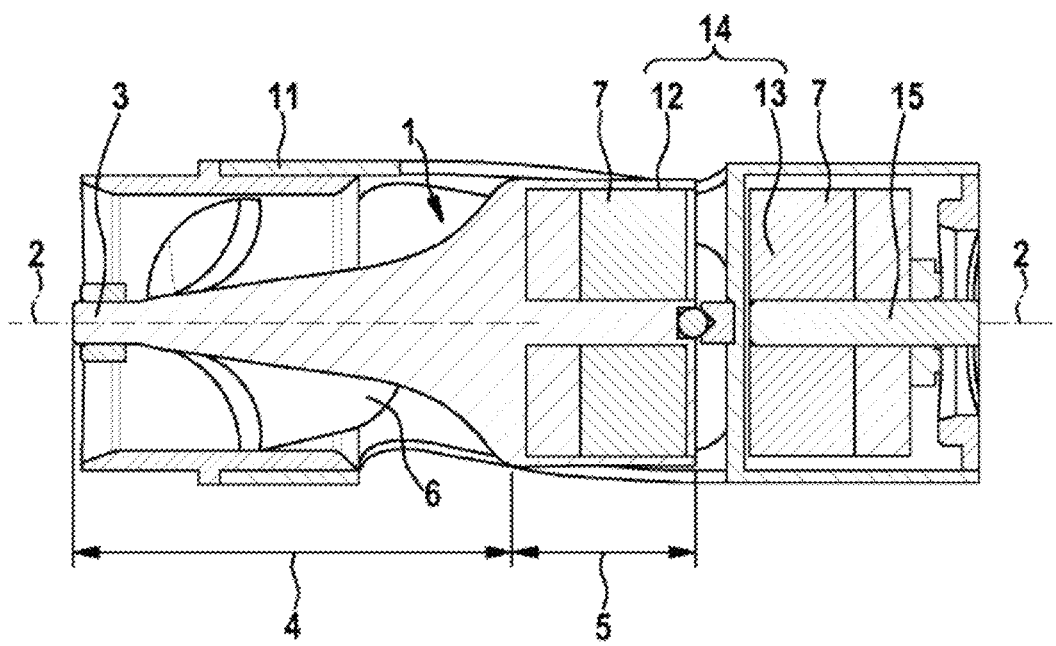
FIG. 2: another here proposed impeller in an impeller housing.

FIG. 2 schematically shows another here proposed impeller 1 in an impeller housing 11. The reference signs are used consistently, so that reference can be made in full to the statements regarding FIG. 1.

The impeller body 3 in FIG. 2 is likewise formed in one piece. The design variant according to FIG. 2 differs from the design variant according to FIG. 1 in particular in that the magnetic coupling 14 in FIG. 2 is formed in the manner of an axial coupling system. For this purpose, the first rotor 12 and the second rotor 13 cooperate accordingly (for axial torque transmission).

FIG. 1 and FIG. 2 show two fundamental options for transmitting the torque from the motor shaft 15 to the impeller 1 without contact using different magnet system arrangements (radial, axial). The transmittable torque depends in particular on one or more of the following factors:

The larger the magnets, the higher the transmittable torque. The magnet size is limited by the available installation space.

The smaller the distance between the magnet systems (motor shaft and impeller), the higher the transmittable torque. The distance results in particular from the wall thickness of the encapsulation and the various gap dimensions.

Arrangement and/or number of magnetic poles.

Material characteristics, such as energy density, remanence, coercive field strength and/or saturation polarization.

Figure 3:
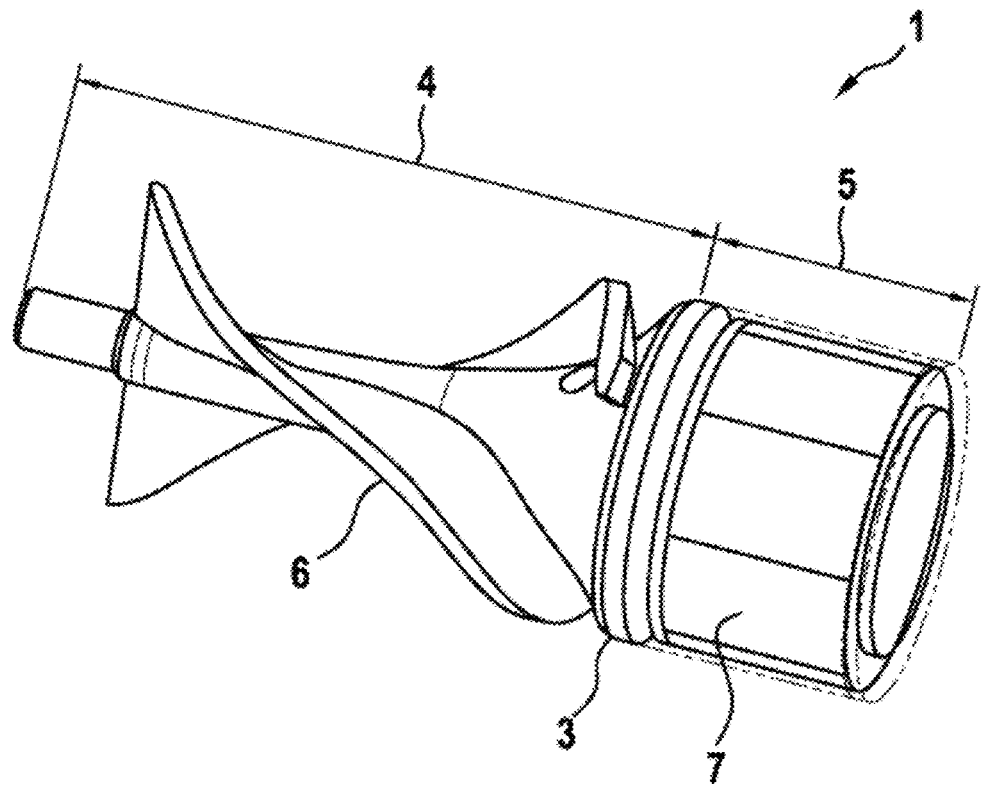
FIG. 3: a here proposed impeller.

FIG. 3 schematically shows a here proposed impeller 1. The reference signs are used consistently, so that reference can be made in full to the statements regarding the preceding figures.

FIG. 3 shows an example of a finally assembled impeller 1 for an 8-pole radial coupling in a perspective view. The impeller body 3 in FIG. 3 is likewise formed in one piece.

Figure 4:
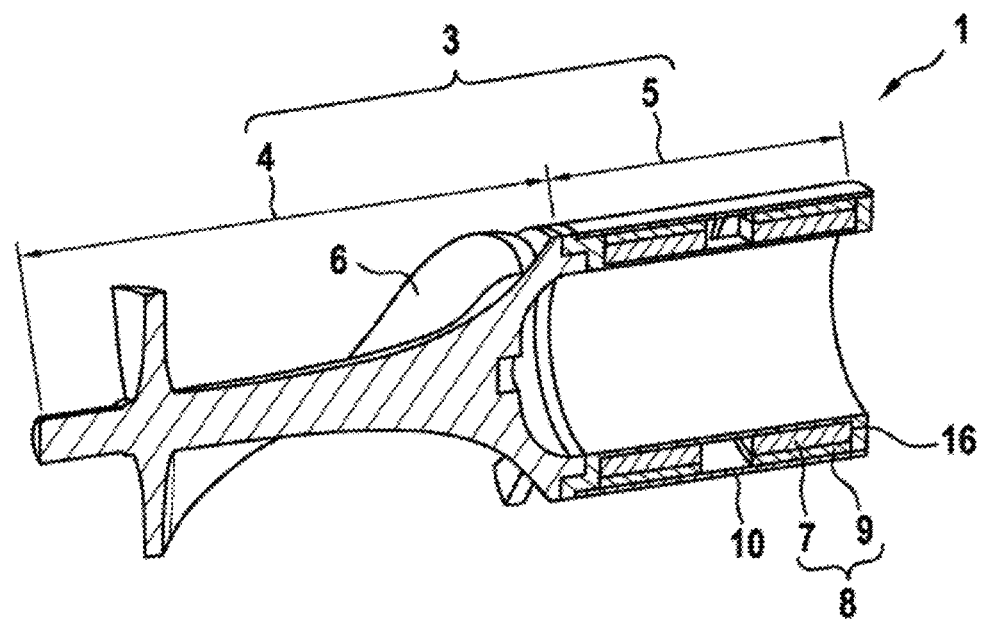
FIG. 4: a sectional view of another here proposed impeller.

FIG. 4 schematically shows another here proposed impeller 1. The reference signs are used consistently, so that reference can be made in full to the statements regarding the preceding figures.

In FIG. 4, the impeller body 3 is formed in multiple parts. For this purpose, the first longitudinal portion 4 and the second longitudinal portion 5 of the impeller body 3 are initially provided as separate or discrete components and then (fixedly) connected to one another to form the impeller body 3.

According to the illustration according to FIG. 4, the second longitudinal portion 5 forms a magnet mount 16, in which the at least one magnet 7 is disposed and encapsulated. As an example, the magnet 7 here is a component of a magnet assembly 8, which comprises the magnet 7 and a magnetic return 9. A cover 10, which (hermetically) closes the magnet mount 16, contributes to the encapsulation.

Figure 5:
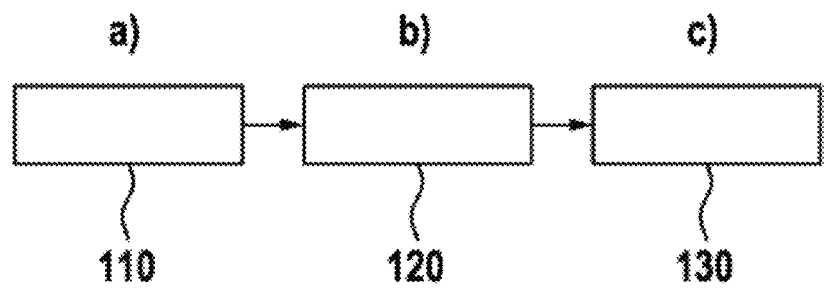
FIG. 5: a sequence of a here proposed method.

FIG. 5 schematically shows a sequence of a here proposed method. The method is used to produce an impeller for an implantable vascular support system. The shown sequence of the method steps a), b) and c) with blocks 110, 120 and 130 is only an example and can be the result of a regular operating sequence. In Block 110, an impeller body is provided, which has a first longitudinal portion and a second longitudinal portion and wherein at least one blade is formed in the first longitudinal portion and configured to axially convey a fluid by means of a rotational movement. In Block 120, at least one magnet is provided. In Block 130, the magnet is disposed and encapsulated in the second longitudinal portion.

Figure 6:
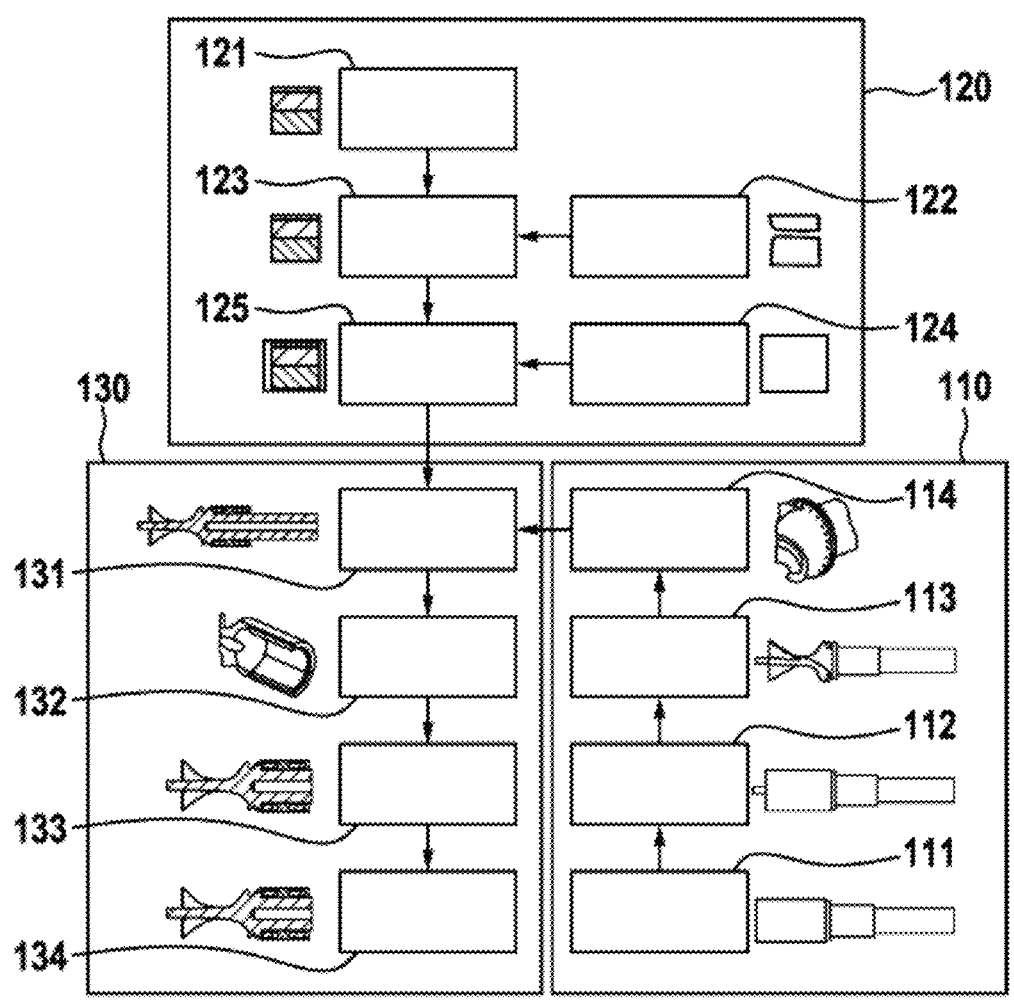
FIG. 6: a sequence of a further here proposed method.

FIG. 6 schematically shows a sequence of a further here proposed method. The method according to FIG. 6 is based on the sequence shown in FIG. 5, wherein examples of the configurations of the method steps a), b) and c) with blocks 110, 120 and 130 are explained in more detail. The method according to FIG. 6 is used to produce an impeller 1 with a one-piece impeller body 3, which can be driven with radial (contactless) torque transmission.

In Block 110, an impeller body is provided with a first longitudinal portion and a second longitudinal portion, wherein at least one blade is formed in the first longitudinal portion and configured to convey a fluid axially with a rotational movement. In other words, it can also be said that, in Block 110, an impeller assembly is provided.

For this purpose, a base body is turned and, if necessary, ground in a Block 111. The impeller or the impeller body is subsequently rough turned in a Block 112. Then, in a Block 113, the impeller or the impeller body, in particular the at least one blade, is milled. Subsequently, flushing bores are drilled as an example here in a Block 114. The flushing bores establish a connection between the main blood flow outside and the blood gap inside the impeller and contribute to a continuous exchange of the blood in the gap geometries, in order to prevent thrombus formation and the occurrence of blood damage mechanisms. The bore diameters are advantageously between 0.2 and 0.8 mm. This is an example that, as in Step a), the impeller body can be provided in one piece.

In Block 120, at least one magnet is provided. In other words, it can also be said that, in Block 120, a magnet system assembly is provided.

For this purpose, the magnets are segmented and magnetized (possibly, even ahead of time) in a Block 121. Furthermore, in a Block 122, a magnetic return is turned and ground. The magnets and the magnetic return are then glued in a Block 123. A sleeve (cover) is subsequently turned in a Block 124. The magnet system is then joined to the sleeve (e.g. by gluing and/or press-fitting) in a Block 125. This is an example that, as in Step b), a magnet assembly can be provided, which comprises the at least one magnet and a magnetic return. In the case of a system without a magnetic return, Blocks 122 and 123 can be omitted.

In Block 130, the magnet is disposed and encapsulated in the second longitudinal portion. In other words, it can also be said that, in Block 130, an overall system assembly is provided.

For this purpose, the magnetic system (from Block 120) is joined to the impeller or the impeller body (from Block 110) in a Block 131. The magnet or the magnet system is encapsulated with the cover (sleeve). The joints are subsequently welded tight (radially and axially) in a Block 132. The clamping spigot is then removed in a Block 133. The clamping spigot is kept in place until Block 133 for handling reasons.

The inner geometry of the impeller body is then turned out in a Block 134. To hollow out the inner geometry by machining, the clamping spigot is first removed (Block 133). The entire system is now held on the welded sleeve. Since the assembly is already assembled, the inner wall thickness (made here of titanium, for example) can also be very thin (wall thickness here approx. 0.1 mm, for example).

Figure 7:
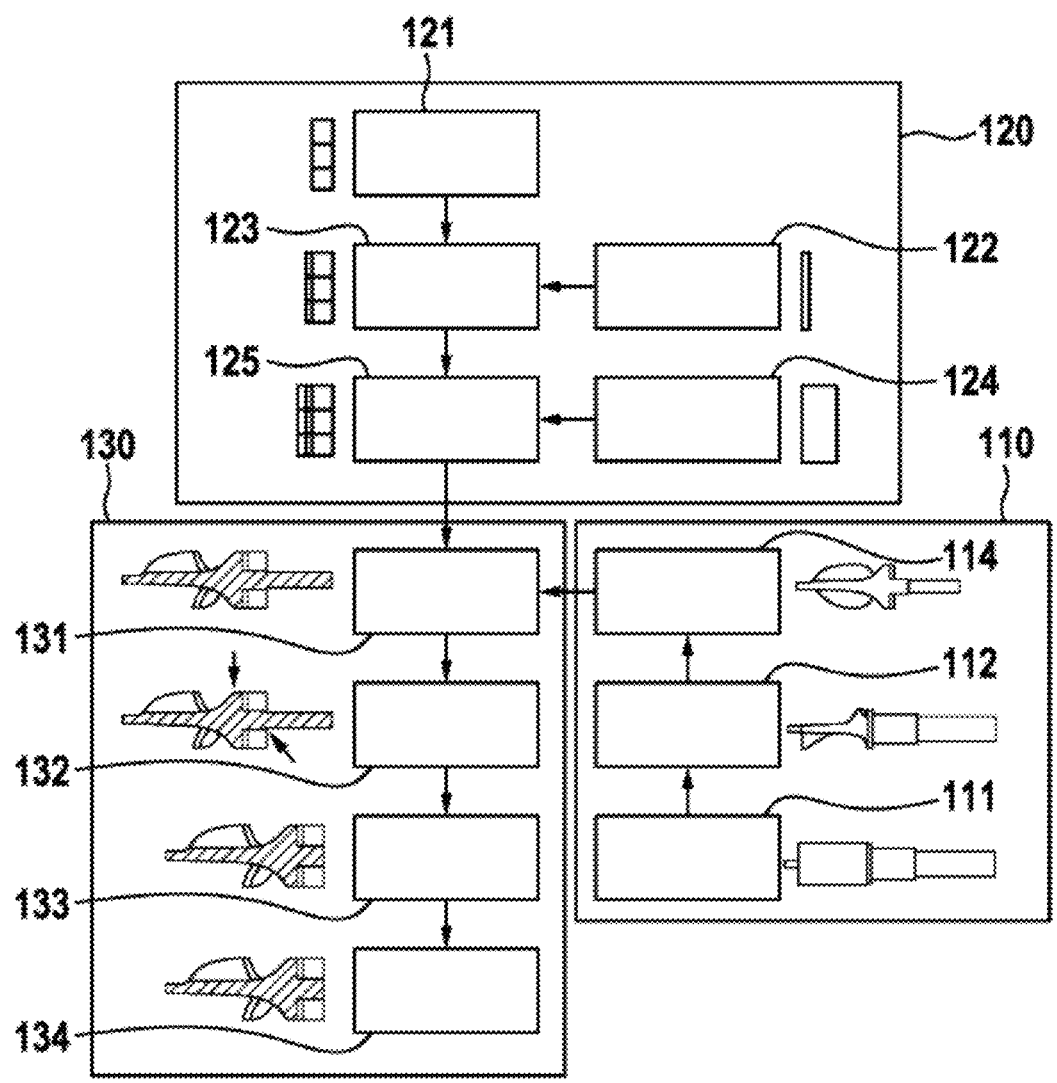
FIG. 7: a sequence of a further here proposed method.

FIG. 7 schematically shows a sequence of a further here proposed method. The method according to FIG. 7 is based on the sequence shown in FIG. 5, wherein examples of the configurations of the method steps a), b) and c) with blocks 110, 120 and 130 are explained in more detail. The method according to FIG. 7 is used to produce an impeller 1 with a one-piece impeller body 3, which can be driven with axial (contactless) torque transmission.

In Block 110, an impeller body is provided with a first longitudinal portion and a second longitudinal portion, wherein at least one blade is formed in the first longitudinal portion and configured to convey a fluid axially with a rotational movement. In other words, it can also be said that, in Block 110, an impeller assembly is provided.

For this purpose, the impeller or the impeller body is rough turned in a Block 111. Then, in a Block 112, the impeller or the impeller body, in particular the at least one blade is milled and flushing bores are provided as an example. The flushing bores establish a connection between the main blood flow outside and the blood gap inside the impeller and contribute to a continuous exchange of the blood in the gap geometries, in order to prevent thrombus formation and the occurrence of blood damage mechanisms. The bore diameters are advantageously between 0.2 and 0.8 mm. The impeller body, in particular the second longitudinal portion of the impeller body, is then turned to a magnet diameter in a Block 114. This is an example of how the impeller body can be provided in one piece in Step a).

In Block 120, at least one magnet is provided. In other words, it can also be said that, in Block 120, a magnet system assembly is provided.

For this purpose, the magnets are segmented and magnetized in a Block 121 (or even earlier). Furthermore, in a Block 122, a magnetic return is turned. The magnets and the magnetic return are then glued, for example, in a Block 123. A sleeve (cover) is subsequently turned in a Block 124. The magnet system is then glued to the sleeve in a Block 125. This is an example of how a magnet assembly comprising the at least one magnet and a magnetic return can be provided in Step b). In the case of a system without a magnetic return, Blocks 122 and 123 can be omitted.

In Block 130, the magnet is disposed and encapsulated in the second longitudinal portion. In other words, it can also be said that, in Block 130, an overall system assembly is provided.

For this purpose, the magnetic system (from Block 120) is joined to the impeller or the impeller body (from Block 110) in a Block 131. The magnet or the magnet system is encapsulated with the cover (sleeve). The joints are subsequently welded tight (radially and axially) in a Block 132. The clamping spigot is then removed in a Block 133. The clamping spigot is kept in place until Block 133 for handling reasons.

The inner geometry of the impeller body is then turned out in a Block 134. To hollow out the inner geometry by machining, the clamping spigot is first removed (Block 133). The entire system is now held on the welded sleeve. Since the assembly is already assembled, the inner wall thickness (made here of titanium, for example) can also be very thin (wall thickness here approx. 0.1 mm, for example).

Figure 8:
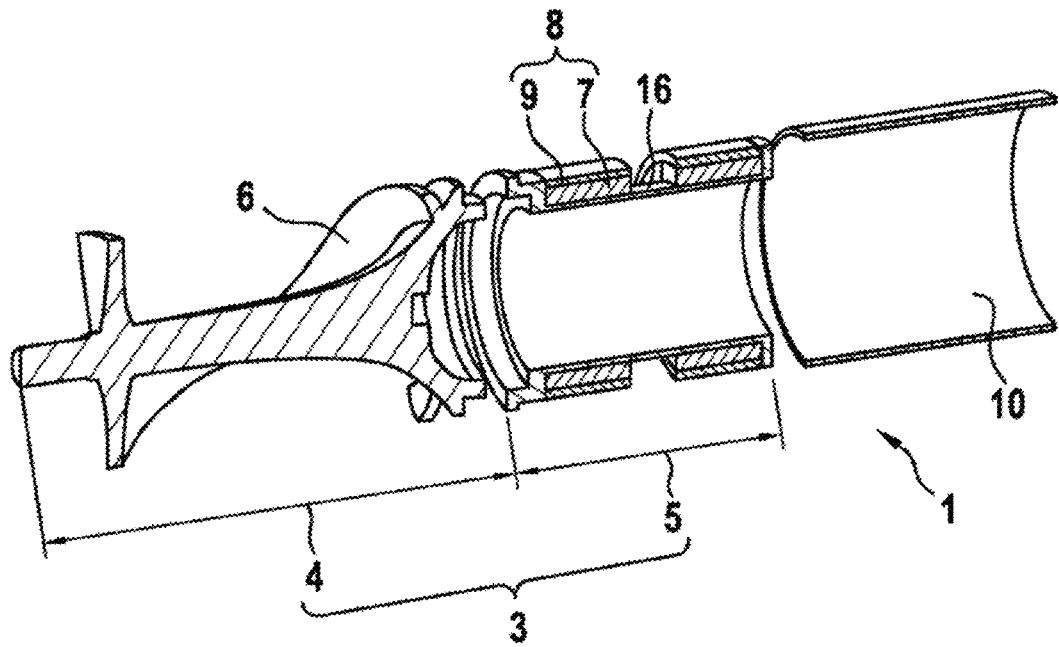
FIG. 8: an illustration of a further here proposed method.

FIG. 8 schematically shows an illustration of a further here proposed method. The reference signs are used consistently, so that reference can be made in full to the statements regarding the preceding figures (in particular FIGS. 1, 2, 3 and 4).

The design variant according to FIG. 8 is an example of how the impeller body 3 can be provided in multiple parts in Step a). In the course of assembly, the magnets 7 can first be joined to the magnet mount 16 (e.g. by gluing). The cover 10 is then pushed on and welded tight. The magnet 7 or the magnet assembly 8 is encapsulated with the cover 10. Finally, the blading 6 is mounted and also welded.

When using ceramics, it is particularly advantageous to apply a metallization in advance in order to be able to connect the parts by means of welding or laser brazing. Glued connections are possible as well, since the connection between the blading 6 and the magnet 7 does not have to be tight.

The multipart nature of the impeller body 3 can be seen clearly in the exploded view of FIG. 8. The cover 10 can be made from a thin-walled tube or wound from a thin sheet metal and welded longitudinally.

Figure 9:
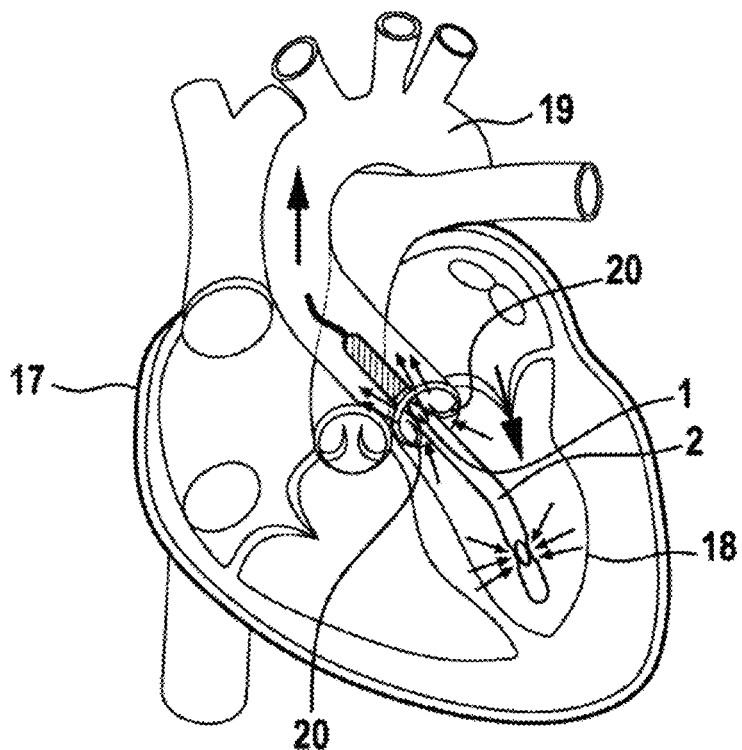
FIG. 9: a support system, implanted in a heart.

FIG. 9 schematically shows a support system 2 implanted in a heart 17. The reference signs are used consistently, so that reference can be made in full to the statements regarding the preceding figures.

FIG. 9 shows a ventricular support system 2, i.e. the support system 2, projecting into a (here left) ventricle 18 of the heart 17. The support system 2 is furthermore disposed in aortic valve position, i.e. the support system 2 intersects a cross-section in which the aortic valves 20 are located. The support system 2 supports the heart 17 by conveying or pumping blood from the ventricle 18 into the aorta 19. The blood flow is indicated in FIG. 9 with arrows.

The support system 2 comprises an impeller 1 (in the manner of an impeller), which is surrounded by a (here not depicted) impeller housing. In the example of an alignment of the support system 2 shown in FIG. 9, the impeller 1 is located in the aorta 19.

The invention claimed is:

1. A cardiac support system, comprising:
   an impeller comprising:
      an impeller body comprising:
         a first longitudinal portion comprising at least one blade configured to axially convey a fluid by a rotational movement; and
         a second longitudinal portion comprising a first rotor extending axially; and
      at least one magnet disposed and encapsulated in the second longitudinal portion; and
   a second rotor extending axially and comprising at least one magnet, wherein the first rotor and the second rotor are configured to form a magnetic coupling, wherein the at least one magnet of the impeller and the at least one magnet of the second rotor partially axially overlap and are partially axially offset, and wherein the at least one magnet of the impeller and the at least one magnet of the second rotor are entirely radially offset.

2. The cardiac support system according to claim 1, wherein the impeller body is a single piece.

3. The cardiac support system according to claim 1, wherein the impeller body comprises multiple pieces.

4. The cardiac support system according to claim 1, further comprising a drive shaft, wherein the drive shaft comprises the second rotor.

5. The cardiac support system according to claim 1, wherein the magnetic coupling comprises a radial coupling.

6. The cardiac support system according to claim 1, wherein the first rotor is an outer rotor and the second rotor is an inner rotor positioned at least partially in a cavity within the impeller body.

7. The cardiac support system according to claim 1, wherein the second longitudinal portion further comprises a magnetic return.

8. The cardiac support system according to claim 1, further comprising a cover configured to at least partially encapsulate the at least one magnet of the second longitudinal portion.

9. The cardiac support system according to claim 1, wherein the at least one magnet of the impeller comprises a plurality of magnets offset from one another axially.

10. The cardiac support system according to claim 1, wherein the at least one magnet of the second rotor comprises a plurality of magnets offset from one another axially.

11. The cardiac support system according to claim 1, wherein:

the second longitudinal portion of the impeller is disposed in a proximal direction with respect to the first longitudinal portion of the impeller; and the at least one magnet of the second rotor is partially axially offset in the proximal direction with respect to the at least one magnet of the impeller.

12. The cardiac support system according to claim 11, wherein said at least one blade of the first longitudinal portion is configured to axially convey said fluid in the proximal direction.

13. A method for producing a cardiac support system, comprising:

disposing and encapsulating at least one magnet in a second longitudinal portion of an impeller body of an impeller of the cardiac support system, wherein the impeller body further comprises a first longitudinal portion comprising at least one blade configured to axially convey a fluid by a rotational movement, wherein the second longitudinal portion comprises a first rotor extending axially, and wherein the cardiac support system comprises a second rotor extending axially and comprising at least one magnet, wherein the first rotor and the second rotor are configured to form a magnetic coupling, wherein the at least one magnet of the impeller and the at least one magnet of the second rotor partially axially overlap and are partially axially offset, and wherein the at least one magnet of the impeller and the at least one magnet of the second rotor are entirely radially offset.

14. The method according to claim 13, wherein the impeller body is a single piece.

15. The method according to claim 13, wherein the impeller body comprises multiple pieces.

16. The method according to claim 13, wherein the second longitudinal portion further comprises a magnetic return.

17. The method according to claim 13, wherein encapsulating the at least one magnet comprises encapsulating the at least one magnet of the second longitudinal portion with a cover.

18. The method according to claim 17, wherein encapsulating the at least one magnet of the second longitudinal portion with the cover comprises thermally joining the cover to the second longitudinal portion.

19. The method according to claim 13, wherein the first rotor is an outer rotor and the second rotor is an inner rotor positioned at least partially in a cavity within the impeller body.

20. The method according to claim 13, wherein the at least one magnet of the impeller comprises a plurality of magnets offset from one another axially.

21. The method according to claim 13, wherein the at least one magnet of the second rotor comprises a plurality of magnets offset from one another axially.

22. The method according to claim 13, wherein:

the second longitudinal portion of the impeller is disposed in a proximal direction with respect to the first longitudinal portion of the impeller; and the at least one magnet of the second rotor is partially axially offset in the proximal direction with respect to the at least one magnet of the impeller.

23. The method according to claim 22, wherein said at least one blade of the first longitudinal portion is configured to axially convey said fluid in the proximal direction.

* * * * *

UNITED STATES PATENT AND TRADEMARK OFFICE
CERTIFICATE OF CORRECTION

| | | |
|---|---|---|
| PATENT NO. | : 11,754,075 B2 | Page 1 of 1 |
| APPLICATION NO. | : 17/258853 | |
| DATED | : September 12, 2023 | |
| INVENTOR(S) | : Armin Schuelke et al. | |

It is certified that error appears in the above-identified patent and that said Letters Patent is hereby corrected as shown below:

On the Title Page

Column 1, under Prior Publication Data, below "US 2021/0379358 A1 ............ Dec. 9, 2021" insert item (30) --Foreign Application Priority Data (DE) 102018211327.0 ............ Jul. 10, 2018--, as new entry.

On Page 8, Column 2, Line 9 under item (56) Other Publications, delete "Artificiai" and insert --Artificial--.

Signed and Sealed this
Eighteenth Day of June, 2024

Katherine Kelly Vidal
*Director of the United States Patent and Trademark Office*